United States Patent
Forejt et al.

(10) Patent No.: US 12,098,984 B2
(45) Date of Patent: Sep. 24, 2024

(54) SUPPLY AIR CONTAMINATION SENSOR

(71) Applicant: Honeywell International Inc., Charlotte, NC (US)

(72) Inventors: Lubos Forejt, Roztoky (CZ); Stephen Yates, South Barrington, IL (US)

(73) Assignee: Honeywell International Inc., Charlotte, NC (US)

( * ) Notice: Subject to any disclaimer, the term of this patent is extended or adjusted under 35 U.S.C. 154(b) by 276 days.

(21) Appl. No.: 17/656,822

(22) Filed: Mar. 28, 2022

(65) Prior Publication Data
US 2022/0316997 A1    Oct. 6, 2022

Related U.S. Application Data

(60) Provisional application No. 63/170,039, filed on Apr. 2, 2021.

(51) Int. Cl.
| | | |
|---|---|---|
| *G01N 1/22* | (2006.01) | |
| *B64D 13/08* | (2006.01) | |
| *B64D 45/00* | (2006.01) | |
| *B64D 13/06* | (2006.01) | |

(52) U.S. Cl.
CPC ........... *G01N 1/2247* (2013.01); *B64D 13/08* (2013.01); *B64D 45/00* (2013.01); *B64D 2013/0688* (2013.01)

(58) Field of Classification Search
CPC .... G01N 1/2247; G01N 1/44; G01N 33/0011; B64D 13/08; B64D 45/00; B64D 2013/0688; B64D 13/06; B64D 13/00; B64F 5/60
See application file for complete search history.

(56) References Cited

U.S. PATENT DOCUMENTS

| | | | | |
|---|---|---|---|---|
| 4,966,005 A | * | 10/1990 | Cowell | B64D 13/06 62/172 |
| 5,750,999 A | | 5/1998 | Fox | |
| 7,803,039 B2 | * | 9/2010 | Inoue | B60H 1/00849 73/23.31 |
| 7,833,305 B1 | * | 11/2010 | Studer | B01D 46/2411 55/467 |
| 8,402,815 B2 | | 3/2013 | Marra | |
| 8,938,973 B2 | | 1/2015 | Dooley et al. | |
| 9,884,281 B2 | * | 2/2018 | Fox | B01D 46/442 |
| 9,957,052 B2 | * | 5/2018 | Fox | B64D 13/06 |

(Continued)

FOREIGN PATENT DOCUMENTS

CN       213892100 U     8/2021

OTHER PUBLICATIONS

Extended Search Report from counterpart European Application No. 22165788.5 dated Aug. 17, 2022, 8 pp.

(Continued)

*Primary Examiner* — Mussa A Shaawat
(74) *Attorney, Agent, or Firm* — Shumaker & Sieffert, P.A.

(57) ABSTRACT

A system configured to be installed in an air flow channel includes a metal surface configured to convert liquid-phase contamination in the air flow channel of a vehicle to vapor-phase contamination; a sensor configured to sense the vapor-phase contamination in the air flow channel; and communication circuitry configured to transmit data indicating sensed levels of the vapor-phase contamination.

20 Claims, 8 Drawing Sheets

(56) References Cited

U.S. PATENT DOCUMENTS

| | | | |
|---|---|---|---|
| 10,035,609 B2* | 7/2018 | Ziarno | B64D 45/00 |
| 10,329,022 B2 | 6/2019 | Fox et al. | |
| 10,955,318 B2 | 3/2021 | Mlcak et al. | |
| 11,179,670 B2 | 11/2021 | Weng et al. | |
| 11,427,334 B2* | 8/2022 | Bartosz | B64D 45/00 |
| 11,465,755 B1* | 10/2022 | Duran | B64D 13/06 |
| 11,893,834 B2* | 2/2024 | Forejt | B64F 5/60 |
| 2007/0084938 A1* | 4/2007 | Liu | F24F 11/77 236/91 D |
| 2008/0283663 A1* | 11/2008 | Space | B64D 13/06 244/118.5 |
| 2009/0084896 A1* | 4/2009 | Boucher | B64D 13/08 454/76 |
| 2013/0030718 A1* | 1/2013 | Williams | G01N 15/0618 702/24 |
| 2016/0214724 A1* | 7/2016 | Fox | B64D 13/06 |
| 2017/0097255 A1 | 4/2017 | Karakaya | |
| 2020/0340889 A1 | 10/2020 | Mlcak et al. | |
| 2020/0340950 A1 | 10/2020 | Mlcak et al. | |
| 2021/0109008 A1* | 4/2021 | Waez | G01N 15/1459 |
| 2021/0172338 A1* | 6/2021 | Beers | F04D 25/04 |
| 2021/0309392 A1* | 10/2021 | Wiegman | B64F 5/60 |
| 2022/0003664 A1 | 1/2022 | Pearce et al. | |
| 2022/0032221 A1* | 2/2022 | Gangloff, Jr. | B64D 13/08 |

OTHER PUBLICATIONS

Overfelt et al., "Sensors and Prognostics to Mitigate Bleed Air Contamination Events," 2012 Progress Report, ACER, Apr. 2012, 52 pp.

U.S. Appl. No. 17/171,896, filed Feb. 9, 2021, naming inventors Kamire et al.

U.S. Appl. No. 17/394,124, filed Aug. 4, 2021, naming inventors Forejt et al.

Response to Extended Search Report dated Aug. 17, 2022, from counterpart European Application No. 22165788.5 filed Oct. 27, 2022, 13 pp.

Notice of Intent to Grant and Text Intended to Grant from counterpart European Application No. 22165788.5 dated Jul. 18, 2023, 41 pp.

* cited by examiner

```
┌─────────────────────────────────┐
│ CONVERT LIQUID-PHASE CONTAMINATION │  ─ 700
│ IN AN AIR FLOW CHANNEL OF A VEHICLE│
│ TO VAPOR-PHASE CONTAMINATION       │
└─────────────────────────────────┘
              │
              ▼
┌─────────────────────────────────┐
│ SENSE THE VAPOR-PHASE           │  ─ 702
│ CONTAMINATION IN THE AIR FLOW   │
│ CHANNEL                         │
└─────────────────────────────────┘
              │
              ▼
┌─────────────────────────────────┐
│ OUTPUT DATA INDICATING SENSED   │  ─ 704
│ LEVELS OF THE VAPOR PHASE       │
│ CONTAMINATION                   │
└─────────────────────────────────┘
```

FIG. 7

SUPPLY AIR CONTAMINATION SENSOR

This application claims the benefit of U.S. Provisional Patent Application No. 63/170,039, filed 2 Apr. 2021, the entire contents of which are incorporated herein by reference.

TECHNICAL FIELD

This disclosure generally relates to systems and methods for monitoring supply air of a vehicle, such as an aircraft.

BACKGROUND

A supply of outside air to a vehicle may become contaminated from artifacts external to the vehicle or from contamination produced by systems internal to the vehicle. For aircraft, example sources of external artifacts that may contaminate an air supply may include exhaust ingestion, pollution, deicing fluid, or engine wash products. Example sources of contamination from internal systems may include fumes or smoke from engine oil, hydraulic fluid, fuel, or the like. The contamination may be associated with elevated concentrations of gaseous compounds, liquid aerosols, or solid particulates in air. Contaminated air in a vehicle may result in an odor in a cabin that can lead to failures such as trip cancellations or passenger dissatisfaction.

SUMMARY

The present disclosure describes example devices, systems, and methods related to detection of supply air contamination. According to one example of this disclosure, a metal surface can be positioned near a contamination sensor. The sensor and the metal surface may be positioned within an air flow channel to sense contamination in the channel.

The metal surface may convert liquid contamination in the channel to vapor-phase contamination. The sensor may be more effective at sensing the vapor-phase contamination, as compared to sensing liquid-phase contamination. Thus, the metal surface may improve the effectiveness of the sensor. When paired with the metal surface, the sensor may have increased longevity because vapor-phase contamination may cause less damage than liquid-phase contamination.

In accordance with another example of this disclosure a system configured to be installed in an air flow channel of a vehicle includes a metal surface configured to convert liquid-phase contamination in the air flow channel of the vehicle to vapor-phase contamination; a sensor configured to sense the vapor-phase contamination in the air flow channel; and communication circuitry configured to transmit data indicating sensed levels of the vapor-phase contamination.

In accordance with another example of this disclosure, a method includes converting, with a metal surface, liquid-phase contamination in an air flow channel of a vehicle to vapor-phase contamination; sensing, with a sensor, the vapor-phase contamination in the air flow channel; and outputting data indicating sensed levels of the vapor-phase contamination.

The details of one or more examples are set forth in the accompanying drawings and the description below. Other features, objects, and advantages will be apparent from the description and drawings, and from the claims.

BRIEF DESCRIPTION OF DRAWINGS

FIG. 7 is a flowchart illustrating example process for sensing contamination in an air flow channel of a vehicle, in accordance with some examples of this disclosure.

DETAILED DESCRIPTION

Figure 1:
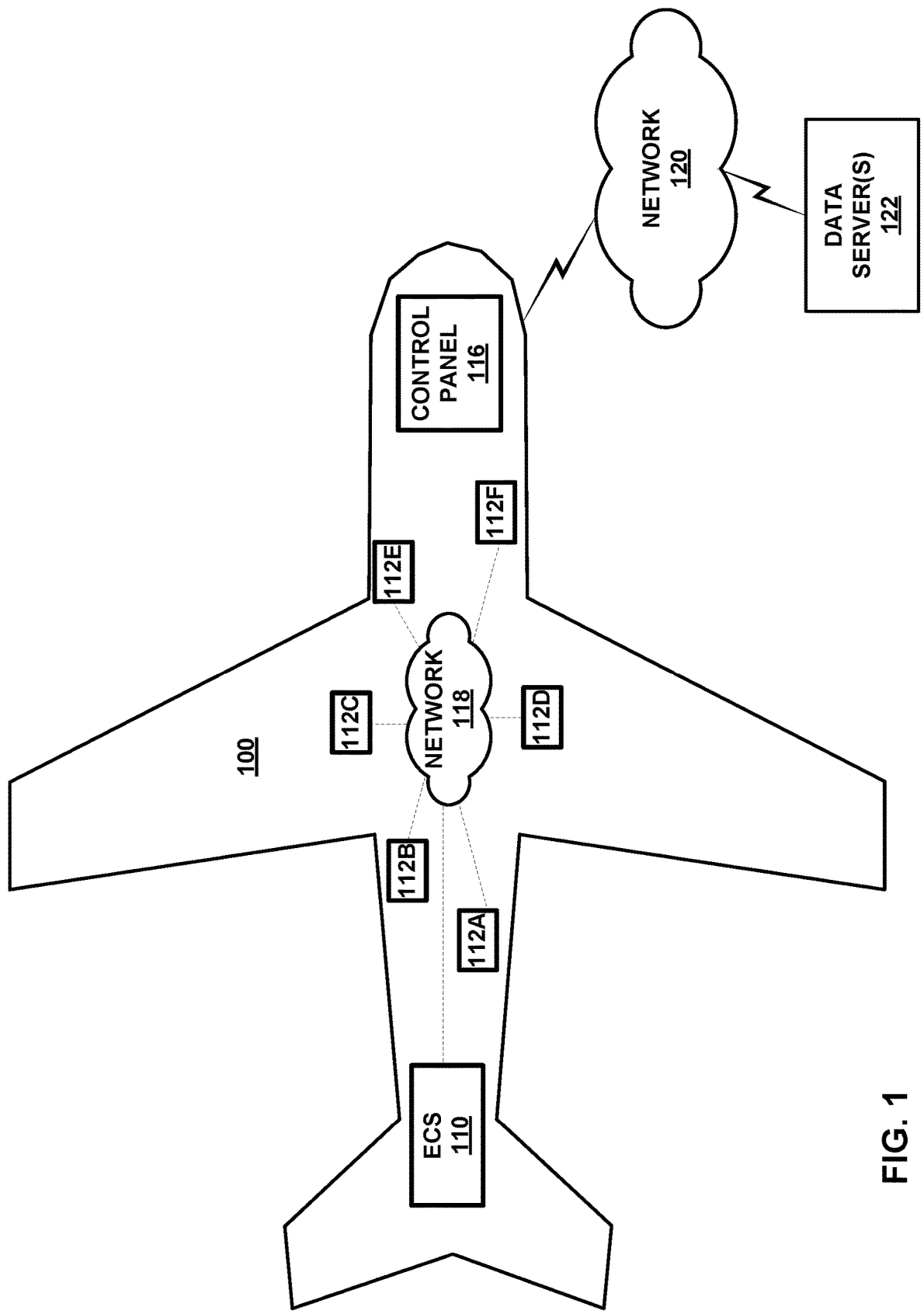
FIG. 1 is a conceptual block diagram depicting an example supply air contamination detection system, in accordance with aspects of this disclosure.

Various examples are described below that are generally directed to apparatuses, methods, systems, and computer program products, that relate to a network of sensing devices affixed to locations within a vehicle, such as an aircraft, a road vehicle, or a marine vessel. While aircraft are primarily referred to herein, in other examples, the example apparatuses, methods, systems, and computer program products described herein may be used with other types of vehicles. Moreover, specific sensor configurations are described, which may be used in vehicle systems or other systems.

The smell(s) in a cabin resulting from external artifacts such as de-icing or exhaust fume ingestion are often indistinguishable from the smell(s) arising due to internal system artifacts such as poor auxiliary power unit (APU) maintenance. Thus, the mere presence of a smell in a vehicle cabin is not necessarily a good indicator of whether the vehicle needs maintenance. Moreover, in instances when a vehicle does need maintenance, the presence of a smell in the vehicle does not necessarily provide much guidance as to what maintenance is needed, or even as to where on the vehicle, or within which subsystem of the vehicle, maintenance is needed.

Many existing vehicles are not equipped with permanent, on-board sensors or detection systems that can detect early-stage issues with air contamination or determine which air pathway, e.g., which air supply line has been contaminated. As used in this disclosure, an air supply line may refer to a line, or fluid pathway, that transports bleed air, supply air, or any other type of air to or from the various subsystems within a vehicle. A duct is one example of an air supply line.

In some cases of bleed air contamination, issues, such as seals starting to leak under specific vehicle conditions, may go unnoticed until a severe leak enables contamination at sufficiently high concentrations to reach the cabin and cause odor during flight. Odor events may lead to trip cancelations or premature landings and stoppages with significant financial cost to the vehicle owners and operators. Such a situation may force a crew to decide whether to divert a flight, which happens as frequently as in 50% of such cases, or continue the flight. Even if a crew elects to continue with a flight, the crew may still need to commence maintenance and troubleshooting after the flight. After the flight, a maintenance crew may inspect all bleed air supply lines (e.g. engines, APU) and examine all possible contaminants but ultimately identify no fault because the source of odor is not present anymore or at only trace amounts that are below a level of detection.

These smell in cabin (SIC) events can cause relatively large disruptions to vehicle operators and business and may cause customer dissatisfaction. This disclosure describes a system that may help diagnose the cause of SIC events relatively early, e.g., before the SIC event is even detectable to humans. Moreover, by understanding the factors that cause, or may in the future cause, a particular SIC event, the techniques of this disclosure may allow a vehicle operator to take appropriate action to prevent recurrence and to minimize the time/cost of unnecessary maintenance interventions. For example, this disclosure describes a system that may identify or help isolate that particular subsystem causing contamination. Additionally, this disclosure describes specific types of sensors and specific sensor configurations that may help enable such functionality.

A system of this disclosure may include one or more sensors capable of sensing parameter values. Although a wide variety of types of sensors may be used to implement the techniques of this invention, by installing the sensors in strategic locations within the vehicle, the techniques of this disclosure may be implemented using relatively simple sensors. For example, instead of using more complicated sensors that are specifically tuned to sense compounds of a particular substance, such as gasoline or deicing fluid, the techniques of this disclosure may be implemented using sensors that are configured to generate an output indicative of total volatile organic compound (TVOC) levels. That is, the parameter values obtained by the sensors may be TVOC levels or changes in TVOC levels. In other implementations, however, the one or more sensors may, for example, be configured to detect other specific parameters, e.g., specific types of VOCs and mixtures, representative of bleed air contamination sources, such as carbon monoxide, engine oil, deicing fluid, hydraulic fluid, exhaust fumes, fuel fumes, engine wash products, and the like.

The one or more sensors may be installed within a vehicle at specific locations. For example, multiple bleed air supply lines within the vehicle may have an installed sensor. Examples of such locations include positions downstream of a left engine, downstream of a right engine, downstream of an APU, downstream of a left environmental control system (ECS) pack discharge, downstream of right ECS pack discharge, downstream of a low pressure ground port supply, or downstream of a high pressure ground port supply. The sensor positions that are downstream of an engine may be upstream of an intersection with another engine line and/or an APU line. In some cases, aircraft that have multiple left engines, multiple right engines, multiple APUs, multiple left ECS pack discharges, multiple right ECS pack discharges, multiple low pressure ground port supplies, or multiple high pressure ground port supplies may utilize additional sensors, such that each subsystem has a dedicated sensor.

The one or more sensors may be configured to monitor, periodically in real-time, multiple air supply lines for the vehicle to collect values for the sensed parameters. One or more sensors may store and/or transmit sensor data that represents values for these sensed parameters. The sensors may additionally be configured, for example, to associate a value for a sensed parameter with a timestamp that identifies the time of measurement. Each sensor of the one or more sensors may also have a unique identifier, such as a name or identification number, such that the sensor data can be associated with the particular sensor that collected that sensor data. Thus, in addition to the values for the sensed parameters, the sensor data may also include timestamp data and an identification of the sensor that captured the parameter values.

A system of this disclosure may enable predictive maintenance by sensing even very small amounts of contamination, regardless of whether the contamination is liquid or gas. Changes in the concentrations of bleed air contaminants can indicate engine problems, and an amplified TVOC sensor may be much more sensitive than other approaches. The sensor may be able to detect low TVOC, high ultra-fine particles by vaporizing the particles.

Other approaches for detecting contamination in bleed air, such as lubrication oil decomposed products in APU supply air, include olfactory senses by crewmembers of a vehicle, an ultrafine particulate sensor, a very sensitive selective or speciating sensor, a speciating portable sensor, a speciating or fingerprint sensor in the vehicle cabin, and a metal oxide TVOC sensor array. In this context, a speciating sensor refers generally to a sensor that can determine a concentration of a specific chemical. The olfactory senses of crewmembers combined with troubleshooting before and during travel (e.g., on ground and in flight) can be used to detect contamination. Using crewmember sense of smell can result in large expenses due to removing vehicles from service and troubleshooting, even when there is no actual contamination.

Another option for detecting contamination is an ultrafine particulate sensor, which can be expensive, large, heavy, and may require air conditioning for pressure and temperature. A very sensitive selective or speciating sensor may be able to differentiate even small differences in concentrations of specific gaseous compounds relevant to pyrolysis/hydrolysis of engine oil, which can increase cost, large, weight, and require air conditioning for pressure and temperature and in some cases pure (e.g., clean and dry) carrier gas. A speciating portable sensor can be a useful diagnostic tool to investigate a SIC event after such an event has been reported.

A speciating or fingerprint sensor located within the vehicle cabin can differentiate different types of events. However, since the system is located in the cabin, the system may be able to provide recommendations of maintenance activities. In addition, the speciating or fingerprint sensor may not provide an early indication of contamination.

A metal oxide TVOC sensor array can be permanently installed at critical points on the airframe. This approach can offer a wider prognostic, health, and maintenance system to reduce costs, and integration of the sensors into components within the vehicle can result in more effective detection. However, some sensors may be insensitive to liquid-phase VOC concentrations. Thus, when the APU bleed air becomes contaminated, the sensor may only detect the gas phase VOC concentration. A large proportion of contaminant mass may be present in the form of aerosol ultrafine and fine particulates. For detection of some contamination events, an additional array of specific-gas detection sensors and/or ultra-fine particle detection sensors may be used to detect some contamination events.

One or more of the sensors in a system of this disclosure may be positioned near a device with a metal surface that converts liquid contamination to vapor-phase contamination. The metal surface of the device, when heated, causes the liquid-phase contamination to change to vapor-phase contamination. Thus, the device with the metal surface may cause vapor-phase contamination, instead of liquid contamination, to reach the sensor. As some sensors may be more effective at sensing the vapor-phase contamination, as compared to sensing the liquid-phase contamination, a device with a metal surface as described in this disclosure may improve the performance of a sensor system when compared to a sensor without such a device, enabling the sensor to be more effective at monitoring contamination levels. Moreover, compared to vapor-phase contamination, the presence of liquid-phase contamination can damage and degrade sensors. Thus, a device for converting liquid contamination to gas contamination, as described herein may improve sensor longevity.

FIG. 1 is a conceptual block diagram of an example supply air contamination detection system in which vehicle 100 includes a plurality of sensors, shown in FIG. 1 as remote sensors 112A-112F (collectively remote sensors 112). Although FIG. 1 shows six remote sensors, vehicle 100 may include a greater or a fewer number of remote sensors in other examples, such as two, three, four, five, or more than six sensors. Any or all of sensors 112 may include the mesh shown in FIGS. 4A and 4B. Vehicle 100 also includes ECS 110 and control panel 116, which are configured to communicate with each other and with sensors 112 over network 118.

Although shown in FIG. 1 as having a fixed-wing form factor, vehicle 100 generally represents any sort of vehicle, and although the techniques of this disclosure may be used in conjunction with any sort of vehicle, the techniques described herein may be of particular benefit for passenger vehicles that include a cabin for passenger travel. Although various techniques of this disclosure will be described with respect to a passenger cabin of an airplane, it should be understood that the techniques are equally applicable to other compartments of other vehicles.

Remote sensors 112 may be located in any one or more of a location downstream of an engine, a location downstream of an APU, a location downstream of an ECS, such as ECS 110, a location downstream of a low pressure ground port, a location downstream of a high pressure ground port, a location in a bleed duct, or any other such location. In some examples, remote sensors 112 may all be the same type of sensor. That is, all of remote sensors 112 may be configured to sense the same parameter, or even be the same model of sensor. In other examples, remote sensors 112 may not all be the same type, and remote sensor 112A may, for instance, be configured to sense a different parameter than remote sensor 112B. In some implementations, one or more of sensors 112 may be modified to optimize the sensors for specific mounting locations to account for extreme cold, extreme heat, the presence of moisture, or other such considerations.

One or more of sensors 112 may be located near a metal surface configured to convert liquid-phase contamination in an air flow channel to vapor-phase contamination. The one or more of sensors 112 may, for example, be located downstream of the metal surface, such that the metal surface converts the liquid-phase contamination to the vapor-phase contamination prior to the air reaching the one or more of sensors 112.

ECS 110 may, for example, be configured to control the general comfort and safety in the passenger cabin of vehicle 100 by, for instance, circulating conditioned air to the passenger cabin, as well as to various other portions of vehicle 100, such as the flight deck, galleys, other occupied compartments, cargo compartments, electronic equipment bays, and the like. ECS 110 may perform such operations to provide a certain level of air quality in the cabin by, for example, maintaining desired temperatures and humidity levels within the cabin of vehicle 100.

Control panel 116 represents any sort of data processing device configured to receive and process sensor values detected by remote sensors 112. Control panel 116 can be a specialized electronic device, such as an application running on a computing device, e.g., a tablet, or can be integrated into an existing vehicle system, such as a vehicle cabin control system that controls the temperature, lighting, entertainment systems, and other aspects of passenger experience.

Control panel 116 may be configured to detect bleed air contamination to provide an early warning that vehicle maintenance may be needed or desirable. Additionally or alternatively, control panel 116 is configured to identify a particular source, such as an engine or APU, of the bleed air contamination, and thus provide a maintenance crew with guidance as to which subsystem within a vehicle may be the source of the contamination and in need of maintenance. Control panel 116 may be configured to identify a particular cause, such as a pilot error or a mechanical failure, that led to the bleed air contamination, and thus provide a maintenance crew with guidance as to whether maintenance may be needed, and if so, what type of maintenance. Control panel 116 may be configured to determine a type of contaminant source, such as whether the source is an internal contaminant such engine oil or an external contaminant such as exhaust.

Network 118 represents any suitable wired or wireless communications network by which control panel 116 can communicate with remote sensors 112. As examples of wired communications, control panel 116 may communicate with remote sensors 112 over direct wiring, twisted pair, fiber optic cable, coaxial cable, or the like. As examples of wireless communications standards, control panel 116 may communicated with remote sensors 112 using an IEEE 802.11 specification (e.g., WiFi™), an IEEE 802.15 specification (e.g., ZigBee™), a Bluetooth™ standard, or the like. In some instances, network 118 may also include any number of intermediary devices such as routers or switches.

In some examples, ECS 110 may also interface with control panel 116 via a controller of ECS 110. The controller of ECS 110 may, for example, include a computer having processing circuitry and a memory, that is configured to control an air purification subsystem and other subsystems of ECS 110. In some implementations, the controller of ECS 110 and control panel 116 may be highly integrated or even implemented in the same circuit or device.

According to techniques of this disclosure, control panel 116 may be configured to receive sensor data from sensors 112 and process the sensor data to generate an output based on the sensor data. Control panel 116 may determine that a sensed parameter value for a sensor of sensors 112 is indicative of supply air contamination by, for example, comparing the sensed parameter to a threshold value and/or detecting a change (e.g., an absolute increase or decrease or a percentage increase or decrease) in the parameter level (e.g., VOC level) relative to a predetermined baseline, which can indicate contamination of the air supply or an emerging contamination. For example, control panel 116 may determine a sensed parameter value for a sensor of sensors 112 is indicative of supply air contamination by at least determining that the sensed parameter is greater than or equal to an upper threshold value for the sensed parameter or less than or equal to a lower threshold value for the sensed parameter. The thresholds can be predetermined and stored in a memory of any suitable device. In response to determining that the sensed parameter value for the sensor is indicative of supply air contamination, control panel 116 may determine a location associated with the specific sensor of sensors 112 that detected the sensed parameter value indicative of supply air contamination. Control panel 116 may then output, based on the location of the specific sensor, an indication of a specific subsystem or location within vehicle 100 that may be in need of maintenance.

Control panel 116 may also utilize context data when analyzing the sensor data and, based on the context data, determine a likely location or subsystem within the vehicle from which the contamination is emanating. Control panel 116 may additionally or alternatively utilize the context data to determine a likely source for the contamination. For example, control panel 116 may receive context data indicating that vehicle 100 is parked on the ground without the engines running. Based on this context data and based on determining that an APU is running while engines are not running, control panel 116 may be configured to recommend that the APU be inspected.

Control panel 116 may be configured to store, during flight and/or during ground operations, the values for the one or more sensed parameters for the supply air for the vehicle cabin and transmit, either during flight or post flight via network 120, the values for the one or more sensed parameters to data servers 122. Data servers 122, which can include any suitable processing circuitry in some examples, may then process the sensed parameters data obtained from vehicle 100. For example, based on a comparison of the sensed parameters data obtained from vehicle 100 with aggregated sensed parameters data from other vehicles, data servers 122 may analyze the health of vehicle 100 to determine if there is supply air contamination within vehicle 100 that is indicative of a subsystem needing maintenance. If data servers 122, for example, determine that a level of a contaminant detected by a sensor that is downstream from ECS 110 is higher than that detected by other similarly situated sensors for other similarly situated flights, then data servers 122 may output a maintenance recommendation that ECS 110 be inspected.

Network 120 represents any suitable communication links between control panel 116 and data servers 122, including wireless communication links according to a cellular communication standard, such as 4G, 4G-LTE (Long-Term Evolution), LTE Advanced, 5G, or the like, or an IEEE 802.11 specification, an IEEE 802.15 specification (e.g., ZigBee™), a Bluetooth™ standard, or the like. Network 120 may also include any number of wired communication links and include intermediary devices such as routers and switches.

Although various techniques for processing the sensor data of sensors 112 have been described herein as being performed by control panel 116, it should be understood that in some alternate implementations, those techniques may be performed entirely or partially by an external processing device such as data servers 122. Control panel 116 may, for example, collect sensor data from sensors 112 and periodically, either during flight or post flight, transmit the collected sensor data, via network 120, to data servers 122.

In one example use case of the techniques described above, during a deicing procedure, deicing fluid may deposit on entries to a bleed air system. The deposits can heat up and vaporize or burn, which can create a range of compounds in the bleed air, which are not normally present. These compounds may enter the cabin and be inhaled by passengers and crew, but these compounds may not cause a perception of odor. One or more of sensors 112 may be configured to detect TVOC levels or concentrations of key marker compounds, such as glycols, aldehydes, or acetic acid, that are indicative of contamination.

In response to receiving this sensor data from sensors 112, control panel 116 or data servers 122 may determine context data for the sensor data to determine a possible source of the contaminant. If, for example, the context data indicates that the wheels of vehicle 100 were on the ground, a speed of vehicle 100 was zero km/h, and the air temperature outside was suitably low such that deicing fluid was used, then control panel 116 or data servers 122 may determine that deicing fluid was the source of the contamination. Additionally, control panel 116 or data servers 122 may determine if, at the time the sensor data was obtained, certain bleed valves were open or closed, whether an air recirculation system is one on or off, whether an APU was on or off, and other such context information. Based on this additional context data, control panel 116 or data servers 122 may be configured to determine, for example, whether the contamination entered the supply air due to a mechanical failure, maintenance crew error, or pilot error.

In another example use case of the techniques described above, engine oil may leak from a main engine or APU and enter bleed air. The engine oil may heat up and vaporize or burn, creating a range of compounds in bleed air that are not normally present or are only present in very low quantities. The vapor or fumes of burning oil is often reported as being associated with and undesirable odor that may worry passengers. One or more of the sensors 112 may be configured to sense indicators of contamination, such as elevated concentrations of key marker compounds like aldehydes, synthetic fatty acids, aromatics, and the like. In response to receiving this sensor data from sensors 112, control panel 116 or data servers 122 may determine context data for the sensor data to determine a possible source of the contaminant.

Control panel 116 or data servers 122 may be configured to determine if the sensor data was obtained while vehicle 100 was at a top of a climb, a top of a descent, or dry cranking with wheels on the ground, or recently after oil maintenance has been performed, some or all of which may be examples of context data and/or an operational status of vehicle 100. Based on this context data, control panel 116 or data servers 122 may, for example, generate a recommendation to a user (e.g., a maintenance crewmember) to check if there has been recent oil tank over-servicing, if bearing or seals are beginning to fail, if a drain passage is blocked, if a nacelle is improperly vented, if a gearbox is leaking, if an oil filter is leak, if turbine starter is leaking, if an oil transmitter is leaking, if an oil breather vent is failing, or if a PMA external leak is present. This list of recommended maintenance checks may include fewer maintenance checks than a maintenance crew would otherwise need to make, and thus may save a vehicle operator time and money. The generation of a recommended maintenance item by control panel 116 to inspect for one of the issues listed above may be based on additional context data, such as an operational status of an engine, motor, or APU on vehicle 100.

Figure 2:
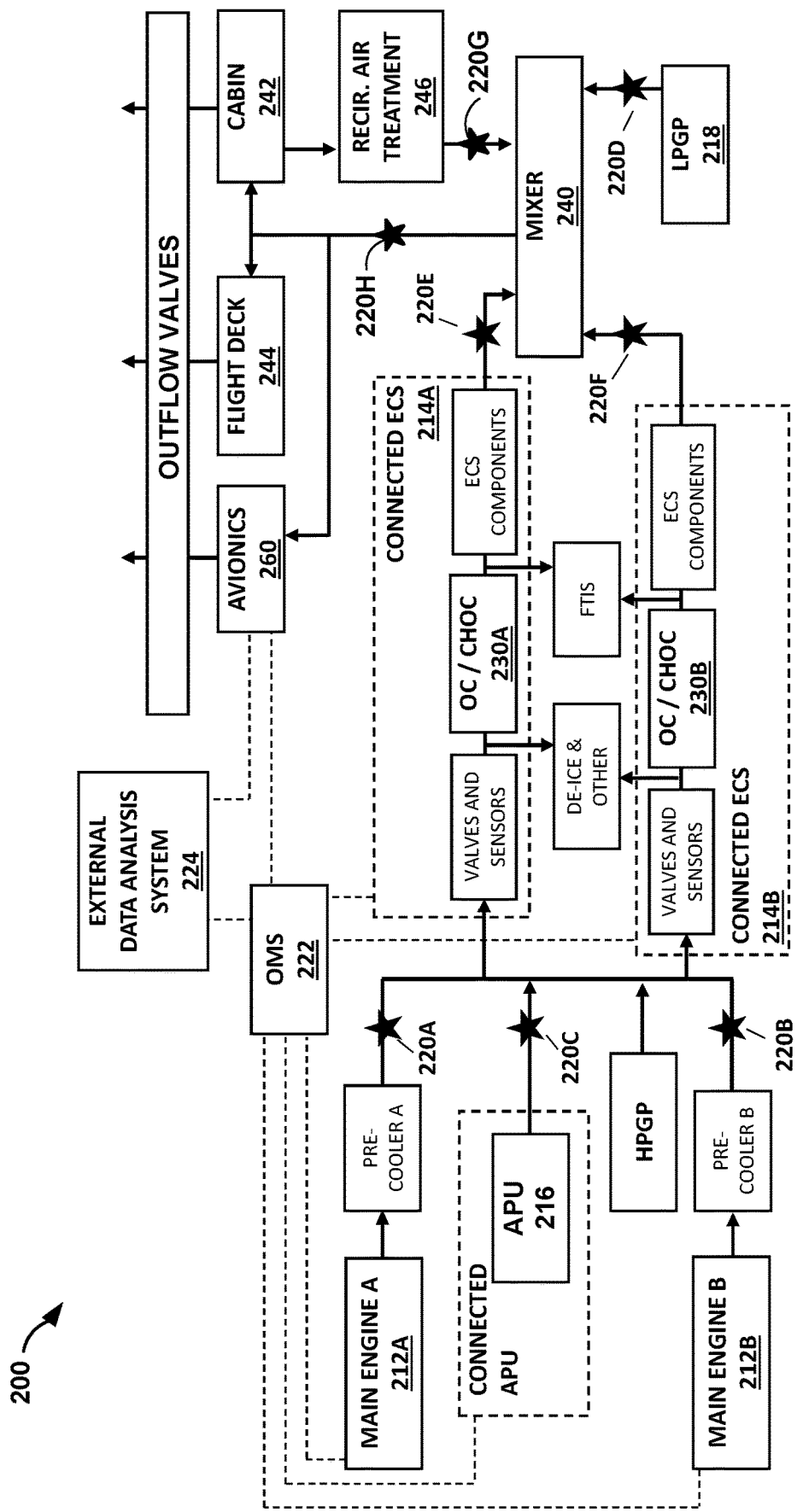
FIG. 2 is a conceptual diagram depicting an example system architecture for a supply air contamination detection system, in accordance with aspects of this disclosure.

FIG. 2 is a conceptual diagram depicting an example system architecture for a supply air contamination detection system within vehicle 200. Vehicle 200 includes multiple subsystems, including main engines 212A and 212B, ECS 214A and 214B, APU 216, LPGP 218, and several other subsystems. In the example of FIG. 2, the stars represent example locations 220A-220F for sensors, such as remote sensors 112 described above with respect to FIG. 1. Locations 220A and 220B represent examples of locations downstream of an engine. Specifically, location 220A is located after a pre-cooler and downstream of a left engine of a main engines 212A and 212B, and location 220B is located after a pre-cooler and downstream of a right engine of a main engines 212A and 212B. Location 220C represents an example of a location downstream of an APU. Location 220C is upstream of the intersection of the line from APU 216 and the line from main engines 212A and 212B. Location 220D represents an example of a location downstream of an LPGP. Locations 220E and 220F (e.g., left pack and right pack) represent examples of locations that are downstream of an ECS. Specifically, location 220E is downstream of ECS 214A (e.g., a left pack), and location 220F is downstream of ECS 214B (e.g., a right pack).

Location 220C may be one example of an especially suitable position for the installation of a device of this disclosure. The outflow air from APU 216 may be cooler than the outflow air from main engines 212. For example, the outflow temperature of APU 216 may be less than 250 degrees Celsius at location 220C, whereas the outflow temperature of main engines 212 may be greater than three hundred degrees Celsius at locations 220A and 220B. Thus, the air flow at location 220C may have a greater proportion of liquid-phase contamination, as compared to the air flow at locations 220A and 220B. For this reason, a device of this disclosure may experience a significant increase in effectiveness when installed at location 220C.

Vehicle 200 also includes on-board maintenance system (OMS) 222, which may generally perform similar functionality to control panel 116, discussed above with respect to FIG. 1. OMS 222 may be configured to transmit sensor data collected by the sensors to external data analysis system 224, which may generally perform similar functionality to data servers 122, discussed above with respect to FIG. 1. External data analysis system 224 may be located outside of the vehicle, and OMS 222 may be configured to communicate with external data analysis system 224.

OMS 222 and/or external data analysis system 224 may be configured to receive data from sensors positioned at any of locations 220A-220F. For example, maintenance crew on the ground may be able to read data on a diagnostic device that wirelessly receives data from the sensors. OMS 222 and/or external data analysis system 224 may be configured to also receive context data from engines 212A and 212B, ECS 214A and 214B, APU 216, and/or avionics 260. OMS 222 and/or external data analysis system 224 may be configured to generate a recommended maintenance item based on the sensor data and the context data. For example, OMS 222 and/or external data analysis system 224 may be configured to generate a recommendation that an oil tank or an oil breather on the vehicle be inspected, that a bearing on the vehicle or a seal on the vehicle be inspected, that a drain passage on the vehicle be inspected for a blockage, that a nacelle on the vehicle be inspected for proper ventilation, or that a gearbox on the vehicle, an oil filter on the vehicle, a turbine starter on the vehicle, or an oil transmitter on the vehicle be inspected for a leak. OMS 222 and/or external data analysis system 224 may be configured to generate a recommendation to perform a specific action with respect to any of the components listed above (e.g., oil tank, oil breather, etc.).

ECS 214A and 214B includes valves and sensors, anti-ice system, fuel tank inerting system (FTIS), ECS components, and ozone converter/combined hydrocarbon and ozone converter (CHOC) 230A and 230B. CHOC 230A and 230B may be referred to as a bleed catalytic converter. As an alternative to CHOC 230A and 230B, vehicle 200 may include a single-purpose ozone converter (OC) for removing ozone by converting ozone molecules to dioxygen molecules. Note, that some aircraft may not be equipped with CHOC or OC.

Mixer 240 may be configured to receive recirculated air from cabin 242 and receive supply air from ECS 214A and 214B and/or LPGP 218. Mixer 240 can mix the air from these two sources and deliver the air to flight deck 244 and cabin 242. One or more sensors may be positioned upstream or downstream from mixer 240. For example, a first sensor may be positioned downstream of ECS 214A and 214B and upstream of mixer 240 (e.g., locations 220E or 220F), a second sensor may be positioned downstream of LPGP 218 and upstream of mixer 240 (e.g., location 220D), a third sensor may be positioned downstream of recirculation air treatment 246 and upstream of mixer 240 (e.g., location 220G), and a fourth sensor may be positioned downstream of mixer 240 (e.g., location 220H). Additional sensor(s) may be positioned in the cabin and/or cockpit of the vehicle.

Figure 3:
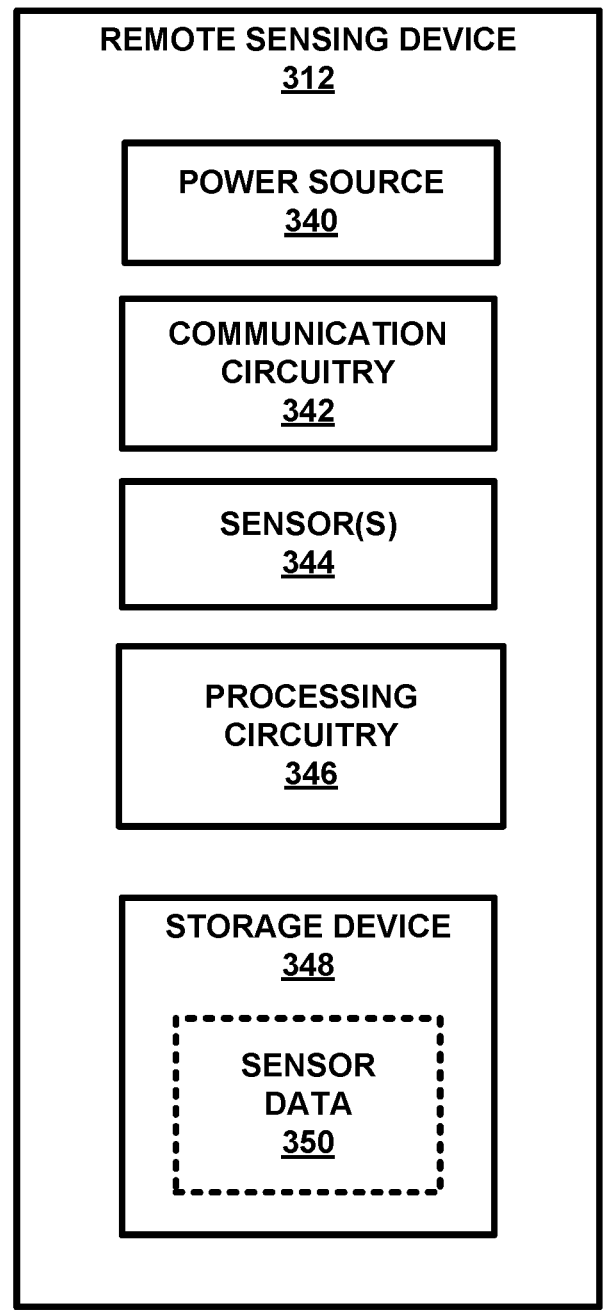
FIG. 3 is a conceptual block diagram of an example remote sensing device.

FIG. 3 is a conceptual block diagram of an example remote sensing device. In the example of FIG. 3, remote sensing device 312 includes power source 340, communication circuitry 342, sensors 344, processing circuitry 346, and storage device 348. Remote sensing device 312 is an example implementation of any of remote sensors 112 described above with respect to FIG. 1. Remote sensing device 312 may be positioned anywhere in a vehicle, including at a location downstream of an engine, a location downstream of an APU (e.g., upstream of the intersection of the APU line and the engine line), a location downstream of an environmental control system, a location downstream of a low pressure ground port, a location downstream of a high pressure ground port, or a location in a bleed duct.

Power source 340 represents all sources of power for the various components of remote sensing device 312 and may include one or more batteries, one or more capacitors, circuitry for receiving alternating current (e.g., 115 volts or 230 volts), or circuitry for receiving direct current (e.g., 28 volts).

Communication circuitry 342 generally represents any one or more of wireless transmitters, wireless receivers, modems, wired networking components (e.g., Ethernet cards), wireless communication components that operate according to any of a variety of IEEE 802.11 standards, or other physical components for facilitating the communication over network 118 described above with respect to FIG. 1.

Sensors 344 generally represent the sensing capabilities of remote sensing device 312 and are configured to sense one or more air quality parameters. For example, sensors 344 may include one or more of a TVOC sensor or other sensors configured to sense compounds such as aldehydes, synthetic fatty acids, aromatics, glycols, acetic acid, or any other such compounds. Sensors 344 include any suitable sensing circuitry configured to sense the parameter of interest. For example, sensors 344 may include any one or more of nondispersive infrared sensors, chemical-based sensors, electromechanical sensors, catalytic bead sensors, photoionization sensors, infrared point sensors, infrared imaging sensors, semiconductor-based sensors, ultrasonic sensors, or holographic sensors.

Processing circuitry 346 generally represents any of the circuitry of remote sensing device 312 needed to carry out any of the functionality described herein, and may include one or more microprocessors, digital signal processors (DSPs), application specific integrated circuits (ASICs), field programmable gate arrays (FPGAs), discrete logic, software, hardware, firmware, or any combinations thereof.

Storage device 348 represents any one or more of read only memory (ROM) or random access memory (RAM), including flash memory, electrically erasable programmable ROM (EEPROM), dynamic random access memory (DRAM), including synchronous DRAM (SDRAM), magnetoresistive RAM (MRAM), resistive RAM (RRAM). Storage device 348 may alternatively or additionally include optical disk storage, magnetic disk storage, or other magnetic storage devices, flash memory, or any other medium that can be used to store desired program code in the form of instructions or data structures and that can be accessed by a computer, such as control panel 116.

Storage device 348 may be configured to store sensor data 350, which represents the sense parameter values obtained by sensors 344. In this regards, storage device 348 may represent a short term, temporary storage, such as a buffer that stores the sensed parameter values prior to transmission by communication circuitry 342, or may represent a longer term, non-volatile storage that that stores the sensed parameter values indefinitely for future processing.

Figure 4A:
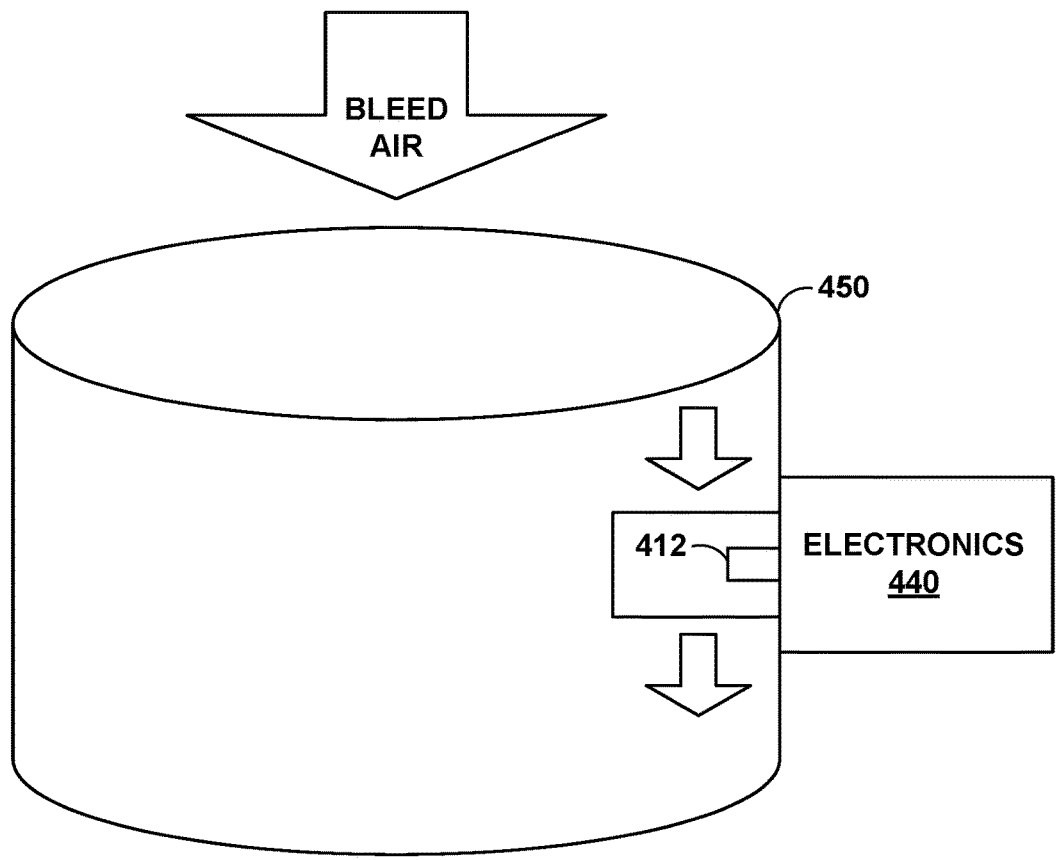
FIGS. 4A and 4B are conceptual block diagrams of an example sensor installed in a pathway for supply air, in accordance with some examples of this disclosure.
Figure 4B:
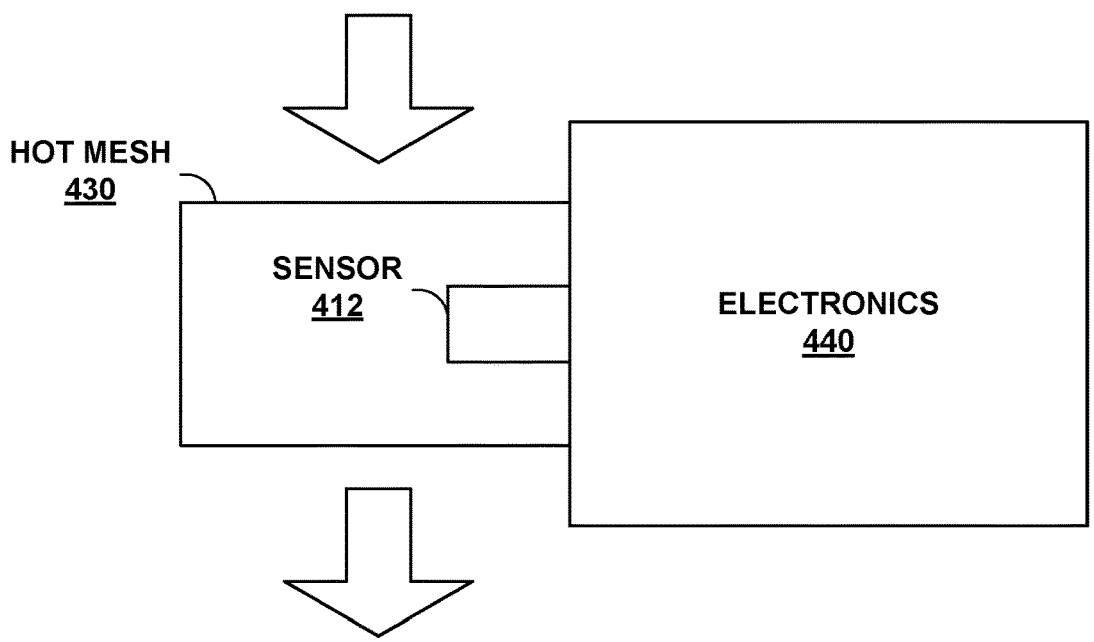

FIGS. 4A and 4B are conceptual block diagrams of an example sensor 412 installed in a pathway for supply air, in accordance with some examples of this disclosure. Sensor 412 may generally be configured with the components and functionality described above with respect to remote sensing device 312 of FIG. 3. In one particular implementation, sensor 412 may include a metal oxide sensor for TVOC detection and may be surrounded by mesh 430. Sensor 412 and mesh 430 may be integrated into a single device, so that the single device can be installed together in air flow channel 450. The single device may be installed when the air flow channel is installed, or mesh 430 may be installed as an aftermarket component after sensor 412 and air flow channel 450 are in operation.

Mesh 430 may include a light weight mesh that, when in operation, can heat to a temperature high enough to vaporize liquid or mist droplets that impinge on mesh 430. The mesh may, for example, heat to 300 to 600 degrees Celsius. In some examples, mesh 430 is just a metal surface that air passes over. In other example, mesh 430 may include subchannels (e.g., openings) for air to pass through near the metal surface of mesh 430. For example, mesh 430 may define a honeycomb structure formed with openings, a rectangular array of openings or other holes, an array of metal sheets parallel to flow, or a metal wool structure. The surrounding high temperature air in the bleed stream may heat mesh 430, or electronics 440 may heat mesh 430 by direct electric resistance heating. Additionally or alternatively, other approaches may be used to heat mesh 430.

A bleed air stream through air flow channel 450 may include vapors and mist droplets. Air flow channel 450 may include a duct in a supply air system onboard a vehicle, such as an aircraft. The bleed air stream passes around and through mesh 430 surrounding sensor 412. Although mesh 430 is shown surrounding sensor 412, mesh 430 may instead be only on one or two sides of sensor 412. For example, mesh 430 may be positioned upstream of sensor 412. The temperature of mesh 430 can be high enough to vaporize the mist in the bleed stream. The mist may be at no risk of igniting because the concentration of organics is too low. The response of sensor 412 to organic compounds may be amplified in examples in which the mist is converted to vapor-phase oil.

One possible side benefit of converting liquid-phase contamination to vapor-phase contamination is that the vapor-phase contamination may be less likely to cause sensor 412 to malfunction. Liquid contamination may be more damaging to sensor 412 than vapor-phase contamination because the liquid can stick to parts of sensor 412, causing sensor 412 to malfunction. Thus, by converting liquid-phase contamination to vapor-phase contamination, mesh 430 may extend the operational lifespan of sensor 412.

Sensor 412 and mesh 430 may be installed near a second sensor that does not have a nearby metal surface. The second sensor may sense only the vapor-phase contamination in air flow channel 450, where none or very little of the liquid-phase contamination is converted to vapor-phase contamination. Both sensors may gather contamination data and transmit the data to a processing system. The processing system may be configured to determine the contamination sensed by each sensor, where sensor 412 may sense a higher level of contamination than the second sensor. Thus, two co-located sensors may provide more information than a single sensor, such as the proportion of liquid- and vapor-phase contamination in air flow channel 450.

In some examples, mesh 430 is coated with an ozone destruction catalyst to avoid a negative response on sensor 412 that masks the VOC concentration. Mesh 430 can be heated by hot bleed stream, but mesh 430 may also have direct electrical resistance heating. The hot metal surface of mesh 430 may also be packed in a flow-through probe (e.g., convection forces) or without flow-through (e.g., diffusion forces).

Mesh 430 may have sufficiently large surface area material and may be installed prior to (e.g., upstream from) sensor 412. Mesh 430 may be able to easily conduct heat using a thin microchannel honeycomb. The material for mesh 430 can be bare metal, metal coated with a suitable catalyst to remove ozone, or other similar materials. For example, mesh 430 may include a metal such as titanium, aluminum, steel, and/or nickel chromium. One possible advantage of extra ozone removal is the increase of TVOC sensor sensitivity in ozone rich supply air. For instance, with a MOS sensor, ozone may produce a negative response, while VOC compounds produce a positive response, which could result in the lack of a detected signal despite the presence of VOCs.

Mesh 430 may be configured to convert (e.g., adsorb, oxidize, vaporize, or change) the liquid form of oil or other VOCs from aerosol droplets into to a vapor phase form of oil and VOCs. Sensor 412 may be configured to then detect the presence of VOCs and generate a sensor signal, whereas sensor 412 may otherwise not be triggered. The pressure drop caused by mesh 430 may be very low. Mesh 430 and sensor 412 may successfully work in temperatures greater than 150 degrees Celsius. Mesh 430 and sensor 412 may not perform as effectively at lower temperatures locations, such as in supply air duct downstream of environmental control system pack. In lower temperature locations, a heating function can be added to mesh 430.

Figure 5:
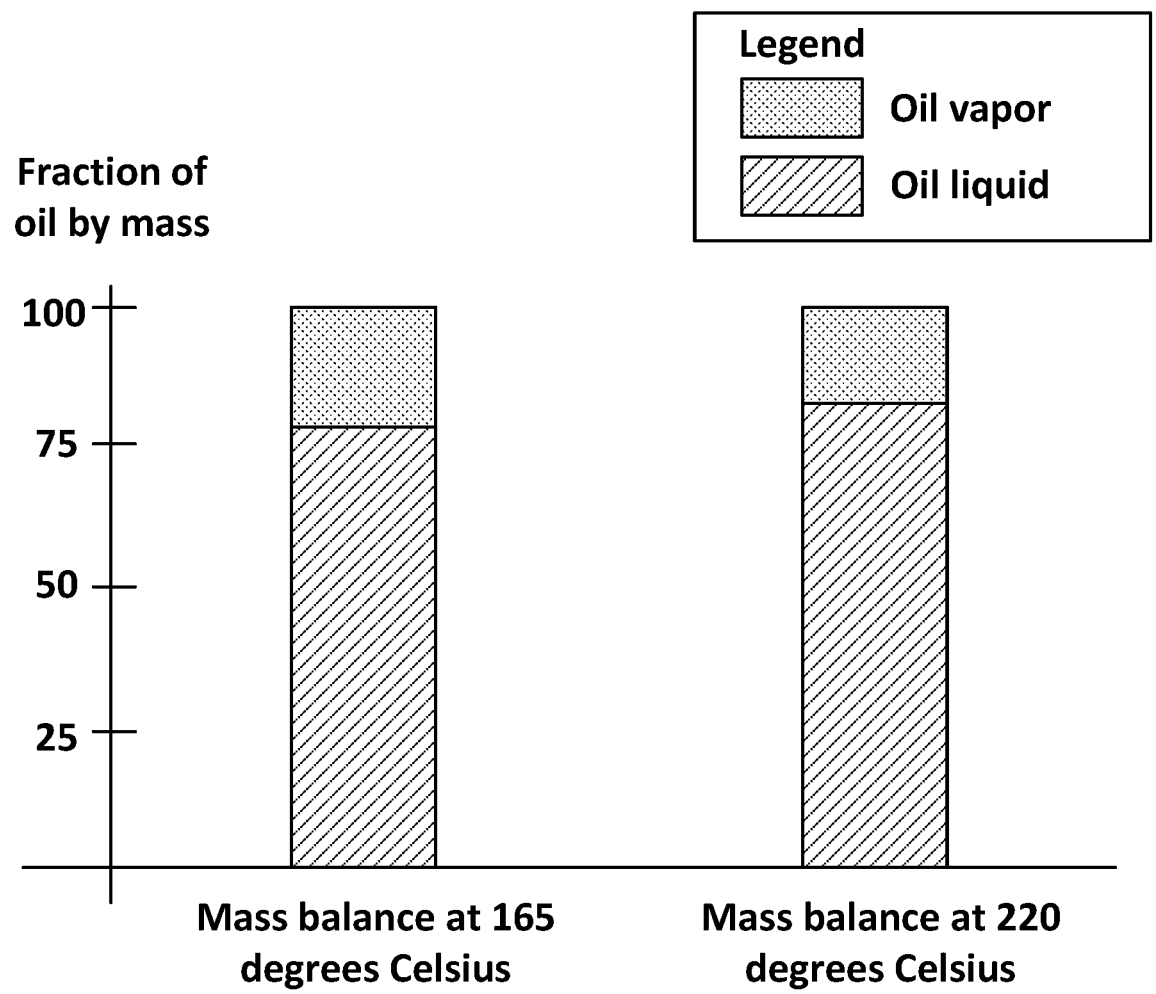
FIG. 5 is a graph of phase fraction of oil by mass at two temperatures.

FIG. 5 is a graph of phase fraction of oil by mass at two temperatures. The majority of oil at 165 and 220 degrees Celsius is in the liquid phase. Less than twenty-five percent of the oil at these temperatures is in the vapor phase. Some VOC sensors may not be able to sense liquid-phase oil as effectively as the VOC sensors can sense vapor-phase oil. Thus, an apparatus that converts liquid-phase oil to vapor-phase oil may increase the effectiveness of a VOC sensor.

At 220 degrees Celsius or lower, engine lubrication oil can be pyrolyzed/hydrolyzed. For example, air from an APU may have temperatures less than or equal to 220 degrees. At these temperatures, the contamination may be predominantly (by mass) in liquid phase form, e.g., in fine and ultra-fine aerosol droplets less than 2.5 micrometer in diameter. Much less of the contamination (by mass) may be in the vapor phase form, e.g., vaporized VOCs.

Figure 6:
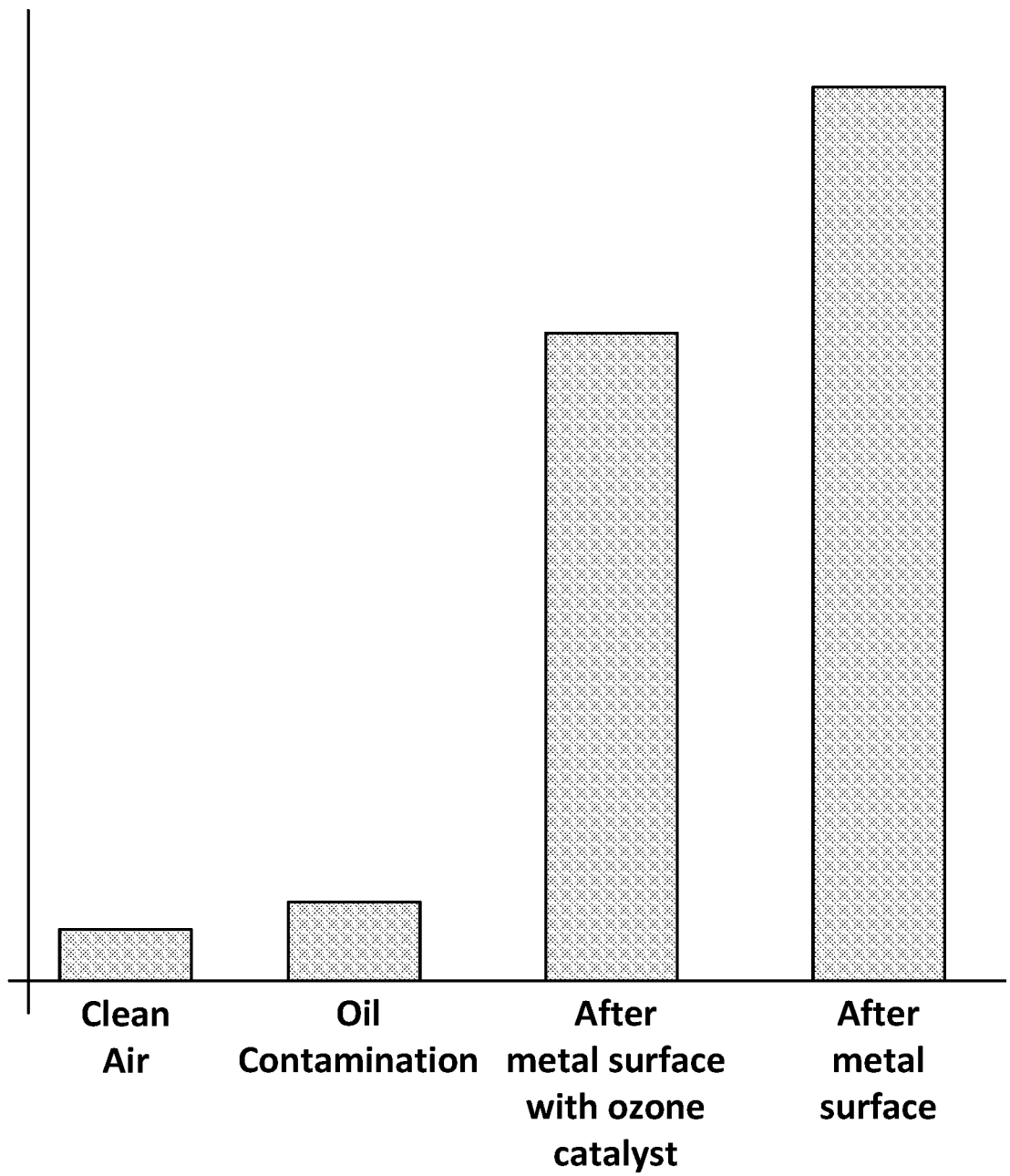
FIG. 6 is a graph of volatile organic compounds in bleed air, in accordance with some examples of this disclosure.

FIG. 6 is a graph of volatile organic compounds in bleed air, in accordance with some examples of this disclosure. As shown in FIG. 6, an example sensor may not sense a large difference between clean air and air contaminated with oil. However, a metal surface placed near and/or upstream of the sensor may increase the amount of TVOC in the air, thus increasing the effectiveness of the sensor.

An example of a non-compound specific total (e.g., sum of individual) VOC type of sensor is a metal oxide sensor. Such a sensor may sense only the vapor-phase portion of the air contaminants. In addition, the sensor may be fouled by droplets of liquid phase contaminants. An ozone catalyst coating on a metal surface may remove and destroy some of the contaminants in the air supply, which may reduce the contamination sensed by the sensor.

FIG. 7 is a flowchart illustrating example process for sensing contamination in an air flow channel of a vehicle. The techniques of FIG. 7 will be described with respect to a sensor system. The sensor system may include a sensor such as one of remote sensors 112, remote sensing device 312, or sensor 412 described above, or some other such sensor. The sensor system may additionally include any of the metal surfaces described above or any other appropriate metal surface.

In the example of FIG. 7, the metal surface of the sensor system converts the liquid-phase contamination in the air flow channel of the vehicle to vapor-phase contamination (700). The sensor senses the vapor-phase contamination in the air flow channel (702). The sensor and the metal surface may, for example, be located relatively near one another at a location within the vehicle. A sensor and a metal surface may be located at various locations within a vehicle, such as at any of locations 220A-220H or some other location within a vehicle. The sensor system outputs data indicating sensed levels of the vapor-phase contamination (704). The sensor system may output the data to a data processing device, such as control panel 116.

Figure 8:
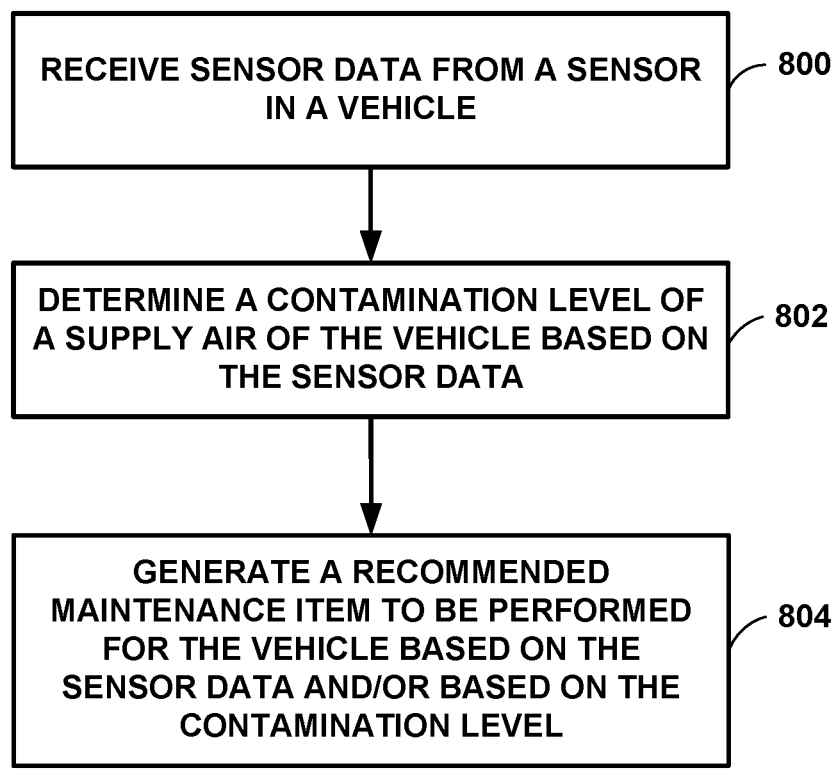
FIG. 8 is a flowchart illustrating example process for generating a recommended maintenance item, in accordance with some examples of this disclosure.

FIG. 8 is a flowchart illustrating example process for generating a recommended maintenance item, in accordance with some examples of this disclosure. The example process of FIG. 8 is described with reference to control panel 116 shown in FIG. 1, although other components may exemplify similar techniques. For example, data servers 122 or OMS 222 shown in FIGS. 1 and 2 may be configured to carry out the example process of FIG. 8, as well as any other steps described herein as being performed by control panel 116 or 416.

In the example of FIG. 8, control panel 116 receives sensor data from one or more of sensors 112A-112F (800). Control panel 116 may receive the sensor data from sensors 112 via network 118. Control panel 116 receive the sensor data as a series of measurements (e.g., sensed parameter values) taken by sensors 112. The sensor data may include a timestamp representing the time at which the sensor data was acquired. Additionally or alternatively, the sensor data may include a potential source location or source component of the contamination. Control panel 116 may also receive context data from another system such as an avionics system, and engine, an APU, an ECS, and/or any other system in vehicle 100. The context data may indicate the current or past status of vehicle 100, an engine or motor on vehicle 100, or an APU on vehicle 100.

In the example of FIG. 8, control panel 116 determines a contamination level of a supply air of vehicle 100 (802). Control panel 116 may be configured to determine a respective contamination level based on data received from each of sensors 112A-112F. For example, control panel 116 can determine a first contamination level for a first location based on data received from sensor 112A, a second contamination level for a second location based on data received from sensor 112B, and so on.

Additionally or alternatively, control panel 116 may be configured to determine the source of the contamination based on the data received from each of sensors 112A-112F. For example, control panel 116 can use the contamination levels at each sensor location to determine the likely source location and/or source type of the contamination. Control panel 116 may be configured to determine whether the contamination source is internal to the vehicle, external to the vehicle, and whether the source type is exhaust, deicing fluid, or oil.

Control panel 116 may be configured to determine that a contamination level satisfies a threshold level by determining that a contamination level is greater than or equal to instantaneous threshold level (e.g., 250 ppb), determining that an average contamination level over a time duration is greater than or equal to a threshold level (e.g., 100 ppb), determining that a contamination level is outside of an acceptable range, and/or determining that a contamination level exceeds a baseline level by more than a threshold amount.

Control panel 116 may be configured to determine whether and to what extent the contamination level exceeds a baseline level. The baseline level may be an indication of the historical level of contamination at a location on the vehicle (e.g., in a specific duct) and/or a geographic location (e.g., latitude and longitude). Control panel 116 may be configured to determine the baseline level based on past measurements from the respective one of sensors 112A-112F. Additionally or alternatively, the baseline level may be a predetermined value that is set during manufacture or a software update, where the predetermined value is based on a fleet-wide or industry-wide acceptable level. The use of a baseline level may allow for the detection of an increase in contamination, even where the sensed contamination level remains below any other threshold level.

In the example of FIG. 8, control panel 116 generates a recommended maintenance item to be performed for vehicle 100 based on the sensor data and/or based on the contamination level (804). Control panel 116 may be configured to select a subset of one or more maintenance items from a set of possible maintenance items. The recommended maintenance item may include a recommendation to inspect a component of ECS 110 or another component on vehicle 100. For example, control panel 116 may be configured to generate a recommendation to inspect an oil tank, bearing, seal, oil breather, drain passage, nacelle, gearbox, oil filter, turbine starter, and/or oil transmitter on vehicle 100. In some examples, the recommended maintenance item may include a rating of the urgency and/or importance of performing the maintenance item. Control panel 116 may be configured to generate an item that recommends no maintenance action but informs the user of an issue that has been identified.

Control panel 116 may be configured to generate a recommended maintenance item based on the location at which contamination was detected. For example, in response to detecting maintenance downstream of an APU and upstream of the engine lines, control panel 116 may be configured to generate a recommendation that the APU be inspected. Thus, control panel 116 may provide information to a technician or other user about how to address the source of any contamination.

Control panel 116 may be configured to present the recommended maintenance item to a user via a display in vehicle 100 and/or via a display external to vehicle 100. The display on vehicle 100 may be part of the avionics system (e.g., where vehicle 100 is an aircraft). Additionally or alternatively, control panel 116 may be configured to transmit an indication of the recommended maintenance item to network 120 and/or data servers 122.

Additionally or alternatively, control panel 116 may be configured to output information about the sensed parameters, such as a contamination level associated with a location in vehicle 100. Control panel 116 may be configured to output other information such as a timestamp and/or context information associated with the contamination level. Control panel 116 may be configured to output the recommended maintenance item including a rating of the urgency and/or importance associated with the item, as well as a timeline, deadline, or date associated with the item. Control panel 116 may be configured to generate a notice of an issue that does not include a corrective action.

Control panel 116 may be configured to also output a category or list of maintenance items for further inspection and/or a location to further inspect. For example, control panel 116 can output a portion of the system that should be inspected, along with a list of the components in that portion of the system. Control panel 116 can select, from a list of items, one or more maintenance items associated with the identified issue so that the technician can check each of the items. Each of these maintenance items may possibly fix the issue, but the technician should check each item to discover whether there are any problems or defects that require maintenance.

The following aspects represent examples of devices, systems, and techniques described above. Although the aspects provide specific combinations of features, it is contemplated that unless stated to the contrary, other combinations of features described in the aspects are also within the scope of this disclosure.

Aspect 1: A device is configured to be installed in an air flow channel. The device includes a sensor configured to sense contamination in the air flow channel. The device also includes a metal surface configured to convert liquid-phase contamination in the air flow channel to vapor-phase contamination.

Aspect 2: The device of the preceding aspect, wherein the metal surface includes a metal mesh.

Aspect 3: The device of the preceding aspects or any combination thereof, wherein the metal surface includes a honeycomb structure.

Aspect 4: The device of the preceding aspects or any combination thereof, wherein the metal surface includes nickel chromium, steel, aluminum, and/or titanium, or any subset or combination thereof.

Aspect 5: The device of the preceding aspects or any combination thereof, wherein the device is configured to be installed in the air flow channel downstream of an auxiliary power unit.

Aspect 6: The device of the preceding aspects or any combination thereof, wherein the device is configured to be installed in the air flow channel downstream of an auxiliary power unit and upstream of an intersection with a line out of an engine.

Aspect 7: The device of the preceding aspects or any combination thereof, further including an ozone catalyst coating on the metal surface.

Aspect 8: The device of the preceding aspects or any combination thereof, wherein the air flow channel is part of a vehicle.

Aspect 9: The device of the preceding aspects or any combination thereof, wherein the air flow channel is part of a supply air system on an aircraft.

Aspect 10: A vehicle system that includes a first sensor implemented in first circuitry, configured to be mounted at a first location within a vehicle, and configured to collect first sensor data for a first sensed parameter and transmit the first sensor data to a processing device; and a second sensor implemented in second circuitry, configured to be mounted at a second location within the vehicle, and configured to collect second sensor data for a second sensed parameter and transmit the second sensor data to the processing device.

Aspect 11: The vehicle system of the preceding aspects or any combination thereof, wherein the first sensor and/or the second sensor are part of a device of aspects 1-9 or any combination thereof.

Aspect 12: The vehicle system of the preceding aspects or any combination thereof, further comprising one or more additional sensors implemented in additional circuitry, configured to be mounted at additional locations within the vehicle, and configured to collect additional sensor data for additional sensed parameters and transmit the additional sensor data to the processing device.

Aspect 13: The vehicle system of the preceding aspects or any combination thereof, wherein one or both of the first sensed parameter and the second sensed parameter includes a measurements of a compound level.

Aspect 14: The vehicle system of the preceding aspect, wherein each of the measurements of compound levels has an associated time stamp.

Aspect 15: The vehicle system of the preceding aspects or any combination thereof, wherein one or both of the first sensor data and the second sensor data includes measurements of TVOC levels.

Aspect 16: The vehicle system of the preceding aspect, wherein each of the measurements of TVOC levels has an associated time stamp.

Aspect 17: The vehicle system of the preceding aspects or any combination thereof, wherein the first sensor data includes an identification of the first sensor or the first location; and/or the second sensor data includes an identification of the second sensor or the second location.

Aspect 18: The system of any of the preceding aspects or any combination thereof, wherein the first sensed parameter is the same as the second sensed parameter.

Aspect 19: The vehicle system of the preceding aspects or any combination thereof, wherein the first location and the second location are each one or more of a location downstream of an engine, a location downstream of an APU, a location down stream of an environmental control system, a location downstream of a low pressure ground port, a location downstream of a high pressure ground port, or a location in a bleed duct.

Aspect 20: The vehicle system of the preceding aspects or any combination thereof, wherein the processing device includes one or more of a system onboard the vehicle, a cloud-based system, a system external to the vehicle, or the first circuitry or the second circuitry.

Aspect 21: A data processing system that includes communication circuitry configured to receive sensor data from one or more sensors mounted in a vehicle; and processing circuitry configured to process the sensor data and generate an output based on the sensor data.

Aspect 22: The data processing system of the preceding aspects or any combination thereof, wherein each respective sensor of the one or more sensors is associated with a respective location within the vehicle, and wherein the processing circuitry is configured generate the output based on a location associated with one of the one or more sensors.

Aspect 23: The data processing system of the preceding aspects or any combination thereof, wherein the one or more sensors include one or more of a sensor located down steam of an engine; a sensor located down stream of an APU; a sensor located down stream of an environmental control system; a sensor located downstream of a low pressure ground port; or a sensor in a bleed duct.

Aspect 24: The data processing system of the preceding aspects or any combination thereof, wherein the processing circuitry is further configured to determine that a sensed parameter value for a sensor of the one or more sensors is indicative of supply air contamination.

Aspect 25: The data processing system of the preceding aspects or any combination thereof, wherein to determine that the sensed parameter value for the sensor is indicative of supply air contamination, the processing circuitry is configured to determine that the sensed parameter is greater than or equal to an upper threshold value for the sensed parameter or less than or equal to a lower threshold value for the sensed parameter.

Aspect 26: The data processing system of the preceding aspects or any combination thereof, wherein in response to determining that the sensed parameter value for the sensor is indicative of supply air contamination, the processing circuitry is further configured to generate the output.

Aspect 27: The data processing system of the preceding aspects or any combination thereof, wherein the processing circuitry is further configured to generate the output in response to other sensors of the one or more sensors mounted in the vehicle determining that a sensed parameter value for the other sensors is not indicative of supply air contamination.

Aspect 28: The data processing system of the preceding aspects or any combination thereof, wherein the output includes an indication of a location associated with the sensor.

Aspect 29: A data processing system that includes communication circuitry configured to receive first sensor data from a first sensor and second sensor data from a second sensor; and processing circuitry configured to: process the first sensor data; process the second sensor data; and generate an output based on one or both of the first sensor data and the second sensor data.

Aspect 30: The data processing system of aspect 29, wherein the first sensor is associated with a first location, and the second sensor is associated with a second location that is different than the first location.

Aspect 31: The data processing system of aspect 29, wherein the processing circuitry is further configured to generate the output based on one or both of the first location or the second location.

Aspect 32: The data processing system of aspects 29-31 or any combination thereof, wherein the first location comprises one or more of a location down steam of an engine, a location down stream of an APU, a location down stream of an environmental control system, or a location downstream of a low pressure ground port.

Aspect 33: A data processing system that includes communication circuitry configured to receive sensor data from a sensor; and processing circuitry configured to: determine a location of the sensor; and generate an output based on the sensor data and the location for the sensor.

Aspect 34: The data processing system of aspect 33, wherein the processing circuitry is further configured to determine context data associated with the sensor data; and generate the output based on the sensor data, the location for the sensor, and the context data.

Aspect 35: The data processing system of any of aspects 33-34, wherein the processing circuitry is further configured to determine a subsystem within the vehicle for which maintenance is recommended based on the location of the sensor.

Aspect 36: The data processing system of any of aspects 33-35, wherein the processing circuitry is further configured to determine a location within the vehicle for which maintenance is recommended based on the location of the sensor.

Aspect 37: A data processing system that includes communication circuitry configured to receive sensor data from a sensor; and processing circuitry configured to: determine context data for the sensor data; and generate an output based on the sensor data and the context data for the sensor data.

Aspect 38: The data processing system of any of aspects 33-37, wherein the context data includes one or more of a pressure in an aircraft when the sensor data was obtained; a pressure outside the aircraft when the sensor data was obtained; an altitude of the aircraft when the sensor data was obtained; a weight on one or more wheels of the aircraft when the sensor data was obtained; a location of the aircraft when the sensor data was obtained; a flight phase, such as on ground, taxing, takeoff, cruising, landing, or at gate, for the aircraft when the sensor data was obtained; weather conditions during a takeoff associated with a flight when the sensor data was obtained; an engine throttle setting; an equipment status for when the sensor data was obtained, such as whether an APU is on or off, whether a bleed valve is opened or closed, an ECS setting; data received by the vehicle during operation of the vehicle; data downloaded after completion of operation of the vehicle; or user input data.

Aspect 39: The data processing system of the preceding aspects or any combination thereof, wherein the output includes one or more of an indication of a type of maintenance that is recommended, an indication of a subsystem within the vehicle for which maintenance is recommended, an indication of a location within the vehicle for which maintenance is recommended, an identification of the sensor, an identification of the location of the sensor, a safety alert, a signal to activate one or more safety systems on the vehicle, a signal to activate a comfort system on the vehicle, or an indication of a most likely source of contamination.

Aspect 40: A method of processing sensor data includes receiving sensor data from one or more sensors mounted in air supply lines of a vehicle; processing the sensor data; and generating an output based on the sensor data.

Aspect 41: A method of processing sensor data includes receiving first sensor data from a first sensor located in a first air supply line of a vehicle; receiving second sensor data from a second sensor located in a second air supply line of the vehicle; processing the first sensor data; processing the second sensor data; and generating an output based on one or both of the first sensor data and the second sensor data.

Aspect 42: A method of processing sensor data includes receiving sensor data from a sensor located in air supply line of a vehicle; determining a location of the sensor; and generating an output based on the sensor data and the location for the sensor.

Aspect 43: A method of processing sensor data includes receiving sensor data from a sensor located in air supply line of a vehicle; determining context data for the sensor data; and generating an output based on the sensor data and the context data for the sensor data.

Aspect 44: The method of any of aspects 40-43, wherein receiving the sensor data comprises receiving the sensor data from the vehicle during a flight of the vehicle.

Aspect 45: The method of any of aspects 40-44, wherein receiving the sensor data comprises receiving the sensor data from the vehicle after a flight of the vehicle, wherein the sensor data was obtained during the flight of the vehicle.

Aspect 46: A system configured to be installed in an air flow channel of a vehicle, the system comprising: a metal surface configured to convert liquid-phase contamination in the air flow channel of a vehicle to vapor-phase contamination; a sensor configured to sense the vapor-phase contamination in the air flow channel; and communication circuitry configured to transmit data indicating sensed levels of the vapor-phase contamination.

Aspect 47: The system of aspect 46, wherein the vehicle comprises an aircraft.

Aspect 48: The system of aspect 47, wherein the air flow channel is part of a supply air system on the aircraft.

Aspect 49: The system of aspect 47 or 48, wherein the device is configured to be installed in the air flow channel downstream of an auxiliary power unit of the aircraft.

Aspect 50: The system of any of aspects 47-49, wherein the device is configured to be installed in the air flow channel downstream of an auxiliary power unit of the aircraft and upstream of an intersection with a line out of an engine of the aircraft.

Aspect 51: The system of any of aspects 46-50, further comprising: a heat source configured to heat the metal surface to cause the metal surface to convert the liquid-phase contamination in the air flow channel of the vehicle to the vapor-phase contamination.

Aspect 52: The system of aspect 51, wherein the heat source comprises bleed air.

Aspect 53: The system of aspect 51 or 52, wherein the heat source comprises a resistive heating element.

Aspect 54: The system of any of aspects 46-53, wherein the metal surface includes one or both of a metal mesh or a honeycomb structure.

Aspect 55: The system of any of aspects 46-54, wherein the metal surface is included in a flow-through probe.

Aspect 56: The system of any of aspects 46-55, wherein the metal surface includes nickel chromium, steel, aluminum, and/or titanium, or any subset or combination thereof.

Aspect 57: The system of any of aspects 46-56, further including an ozone catalyst coating on the metal surface.

Aspect 58: The system of any of aspects 46-57, further comprising: a data processing device comprising: communication circuitry configured to receive the data indicating the sensed levels of the vapor-phase contamination; and processing circuitry configured to process the data and generate an output based on the data.

Aspect 59: The system of aspect 58, wherein the processing circuitry is further configured to generate the output based on a location associated with the sensor.

Aspect 60: The system of aspect 58 or 59, wherein: the communication circuitry is further configured to receive second data from a second sensor in the vehicle; and the processing circuitry is further configured to process the second data and generate the output based on the second data.

Aspect 61: The system of any of aspects 58-60, wherein the output includes one or more of: an indication of a type of maintenance that is recommended, an indication of a subsystem within the vehicle for which maintenance is recommended, an indication of a location within the vehicle for which maintenance is recommended, an identification of the sensor, an identification of the location of the sensor, a safety alert, a signal to activate one or more safety systems on the vehicle, a signal to activate a comfort system on the vehicle, or an indication of a most likely source of contamination.

Aspect 62: A method comprising: converting, with a metal surface, liquid-phase contamination in an air flow channel of a vehicle to vapor-phase contamination; sensing, with a sensor, the vapor-phase contamination in the air flow channel; and outputting data indicating sensed levels of the vapor-phase contamination.

Aspect 63: The method of aspect 62, wherein the vehicle comprises an aircraft.

Aspect 64: The method of aspect 63, wherein the air flow channel is part of a supply air system on the aircraft.

Aspect 65: The method of any of aspects 62-64, wherein the metal surface and the sensor are located in the air flow channel downstream of an auxiliary power unit of the aircraft.

Aspect 66: The method of any of aspects 62-65, wherein the metal surface and the sensor are located in the air flow channel downstream of an auxiliary power unit of the aircraft and upstream of an intersection with a line out of an engine of the aircraft.

Aspect 67: The method of any of aspects 62-66, further comprising: heating the metal surface to cause the metal surface to convert the liquid-phase contamination in the air flow channel of the vehicle to the vapor-phase contamination.

The devices and systems described in the preceding aspects or any combination thereof may correspond to any of data processing systems or other such processing devices described herein.

The various electronic devices described in this disclosure may be implemented as one or more ASICs, as a magnetic nonvolatile RAM or other types of memory, a mixed-signal integrated circuit, a central processing unit (CPU), an FPGA, a microcontroller, a programmable logic controller (PLC), a system on a chip (SoC), a subsection of any of the above, an interconnected or distributed combination of any of the above, or any other type of component or one or more components capable of performing the techniques described herein.

Functions executed by electronics associated with the devices systems described herein may be implemented, at least in part, by hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in electronics included systems described herein. The terms "processor," "processing device," or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, functionality ascribed to the devices and systems described herein may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure. The computer-readable medium may be non-transitory.

Various aspects of the disclosure have been described. These and other aspects are within the scope of the following claims.

What is claimed is:

1. A system configured to be installed in an air flow channel of a vehicle, the system comprising:

a mesh defining a metal surface and configured to continuously convert liquid-phase contamination in the air flow channel of a vehicle to vapor-phase contamination;

an ozone catalyst coating on the metal surface;

a sensor configured to sense the vapor-phase contamination in the air flow channel; and communication circuitry configured to transmit data indicating sensed levels of the vapor-phase contamination.

2. The system of claim 1, wherein the vehicle comprises an aircraft.

3. The system of claim 2, wherein the air flow channel is part of a supply air system on the aircraft.

4. The system of claim 2, wherein the system is configured to be installed in the air flow channel downstream of an auxiliary power unit of the aircraft.

5. The system of the claim 2, wherein the system is configured to be installed in the air flow channel downstream of an auxiliary power unit of the aircraft and upstream of an intersection with a line out of an engine of the aircraft.

6. The system of claim 1, further comprising:

a heat source configured to heat the metal surface to cause the metal surface to convert the liquid-phase contamination in the air flow channel of the vehicle to the vapor-phase contamination.

7. The system of claim 1, wherein the metal surface includes a honeycomb structure.

8. The system of claim 1, wherein the metal surface is included in a flow-through probe.

9. The system of claim 1, wherein the metal surface includes nickel chromium, steel, aluminum, and/or titanium, or any subset or combination thereof.

10. The system of claim 1, further comprising:

a data processing device comprising:

communication circuitry configured to receive the data indicating the sensed levels of the vapor-phase contamination; and processing circuitry configured to process the data and generate an output based on the data.

11. The system of claim 10, wherein the processing circuitry is further configured to generate the output based on a location associated with the sensor.

12. The system of claim 10, wherein:

the communication circuitry is further configured to receive second data from a second sensor in the vehicle; and the processing circuitry is further configured to process the second data and generate the output based on the second data.

13. The system of claim 1, wherein the metal surface is configured to adsorb the liquid-phase contamination, oxidize at least a portion of the liquid-phase contamination into volatile organic compounds, and vaporize the volatile organic compounds to form the vapor-phase contamination.

14. A method comprising:

continuously converting, with a mesh defining a metal surface, liquid-phase contamination in an air flow channel of a vehicle to vapor-phase contamination;

converting, with an ozone catalyst coating on the metal surface, ozone in the air flow channel to dioxygen;

sensing, with a sensor, the vapor-phase contamination in the air flow channel; and outputting data indicating sensed levels of the vapor-phase contamination.

15. The method of claim 14, wherein the vehicle comprises an aircraft.

16. The method of claim 15, wherein the air flow channel is part of a supply air system on the aircraft.

17. The method of claim 15, wherein the metal surface and the sensor are located in the air flow channel downstream of an auxiliary power unit of the aircraft.

18. The method of the claim 15, wherein the metal surface and the sensor are located in the air flow channel downstream of an auxiliary power unit of the aircraft and upstream of an intersection with a line out of an engine of the aircraft.

19. The method of claim 14, further comprising:

heating the metal surface to cause the metal surface to convert the liquid-phase contamination in the air flow channel of the vehicle to the vapor-phase contamination.

20. The method of claim 14, wherein continuously converting the liquid-phase contamination to vapor-phase contamination includes adsorbing the liquid-phase contamination to the metal surface, oxidizing at least a portion of the liquid-phase contamination into volatile organic compounds, and vaporizing the volatile organic compounds to form the vapor-phase contamination.

* * * * *